United States Patent
Naito et al.

(10) Patent No.: US 6,621,838 B2
(45) Date of Patent: Sep. 16, 2003

(54) LASER TREATMENT APPARATUS

(75) Inventors: Yasuyuki Naito, Nukata-gun (JP); Wataru Niwa, Gamagori (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/911,401

(22) Filed: Jul. 25, 2001

(65) Prior Publication Data

US 2002/0018497 A1 Feb. 14, 2002

(30) Foreign Application Priority Data

Aug. 1, 2000 (JP) ......................................... 2000-237637

(51) Int. Cl.[7] ................................................. H01S 3/04
(52) U.S. Cl. ........................................... 372/34; 372/35
(58) Field of Search ..................... 606/15, 31; 378/147, 378/6; 359/13; 356/226; 372/38.08, 35, 34

(56) References Cited

U.S. PATENT DOCUMENTS 5,845,504 A * 12/1998 LeBleu ........................ 62/285
6,002,987 A * 12/1999 Kamiya et al. ............. 250/492.2
6,058,718 A * 5/2000 Forsberg et al. ............... 62/125

FOREIGN PATENT DOCUMENTS

| JP | 05-317352 | * 3/1993 | ............. H01S/3/11 |
| JP | A 5-300948 | 11/1993 | |
| JP | A 7-221373 | 8/1995 | |

* cited by examiner

*Primary Examiner*—Paul Ip
*Assistant Examiner*—Tuan Nguyen
(74) *Attorney, Agent, or Firm*—Oliff & Berridge, PLC

(57) ABSTRACT

A laser treatment apparatus for performing treatments on an affected part by irradiating the affected part with a laser beam for treatment is disclosed. This apparatus includes a laser oscillator, a cooling unit including a fan which cools the laser oscillator, a temperature sensor which directly or indirectly detects a temperature of the laser oscillator, and a control unit which drives the fan at roughly constant low speed when a detected temperature by the temperature sensor is below a predetermined reference value and at roughly constant high speed when the detected temperature is the predetermined reference value or more.

9 Claims, 6 Drawing Sheets

FIG. 6

| CHANG TEMP. (°C) | THE NUMBER OF SHOTS | 30°C→Over (min) | Over→40°C (min) | Over→35°C (min) | Over→30°C (min) |
|---|---|---|---|---|---|
| CONVENTIONAL LINEAR CONTROL | 933 | 6.7 | 4.4 | 8.0 | 14.1 |
| 40 | 977 | 6.9 | 4.2 | 8.0 | 17.0 |
| 45 | 965 | 6.8 | 4.4 | 8.7 | 17.9 |
| 50 | 893 | 6.3 | 4.7 | 9.2 | 18.6 |

LASER TREATMENT APPARATUS

BACKGROUND OF THE INVENTION

1. Field of the Invention

The present invention relates to a laser treatment apparatus for performing treatments on an affected part by irradiating the part with a treatment laser beam.

2. Description of Related Art

There have been conventionally known laser treatment apparatuses for performing treatments on a patient's eye by irradiating a treatment laser beam to the eye. This type of the apparatuses would generate high heat from a laser oscillator, or a laser head. Accordingly, the laser head should be cooled by heat radiation. As a cooling mechanism therefor, there are a forced-air-cooled type and an internal circulation water-cooled type. In the internal circulation water-cooled type, cooling water (coolant) is circulated around the laser head to cool it. The cooling water having increased in temperature due to the heat absorption from the laser head radiates the heat through a radiator. An electric fan is driven to send a current of air to the radiator, so that the radiator is forced to radiate the heat.

In the conventional apparatuses of the forced-air-cooled type and the internal circulation water-cooled type, however, the driving speed of the electric fan is controlled so as to linearly change according to temperatures. This would cause a problem that the fan makes large noises even during regular use where the temperature of the fan is not raised so high.

In particular, the laser treatment apparatus is generally used in an operating room of ophthalmological clinics or hospitals. The apparatus therefore has to control noise caused therefrom in order to eliminate the anxiety of a patient or reduce a burden on an operator.

SUMMARY OF THE INVENTION

The present invention has been made in view of the above circumstances and has an object to overcome the above problems and to provide a laser treatment apparatus capable of reducing noises produced by a cooling fan to thereby improve a treatment environment.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for performing treatments on an affected part by irradiating the affected part with a laser beam for treatment, the apparatus including: a laser oscillator: a cooling unit including a fan which cools the laser oscillator; a temperature sensor which directly or indirectly detects a temperature of the laser oscillator; and a control unit which drives the fan at roughly constant low speed when a detected temperature by the temperature sensor is below a predetermined reference value and at roughly constant high speed when the detected temperature is the predetermined reference value or more.

According to another aspect of the present invention, there is provided a laser treatment apparatus for performing treatments on an affected part by irradiating the affected part with a laser beam for treatment, the apparatus including: a laser oscillator; a cooling water circulation unit including a pipe and a pump which circulate cooling water through the laser oscillator; a radiator provided with a fan for making heat radiation of the cooling water; a water temperature sensor which detects a temperature of the cooling water drained from the laser oscillator after circulation therethrough; and a control unit which drives the fan at roughly constant low speed when a detected temperature by the water temperature sensor is below a predetermined reference value and at roughly constant high speed when the detected temperature is the predetermined reference value or more.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 6 is a table showing measurement results of cooling capacity according to differences in temperatures at which the fan voltage is changed.

DETAILED DESCRIPTION OF THE PREFERRED EMBODIMENTS

Figure 1:
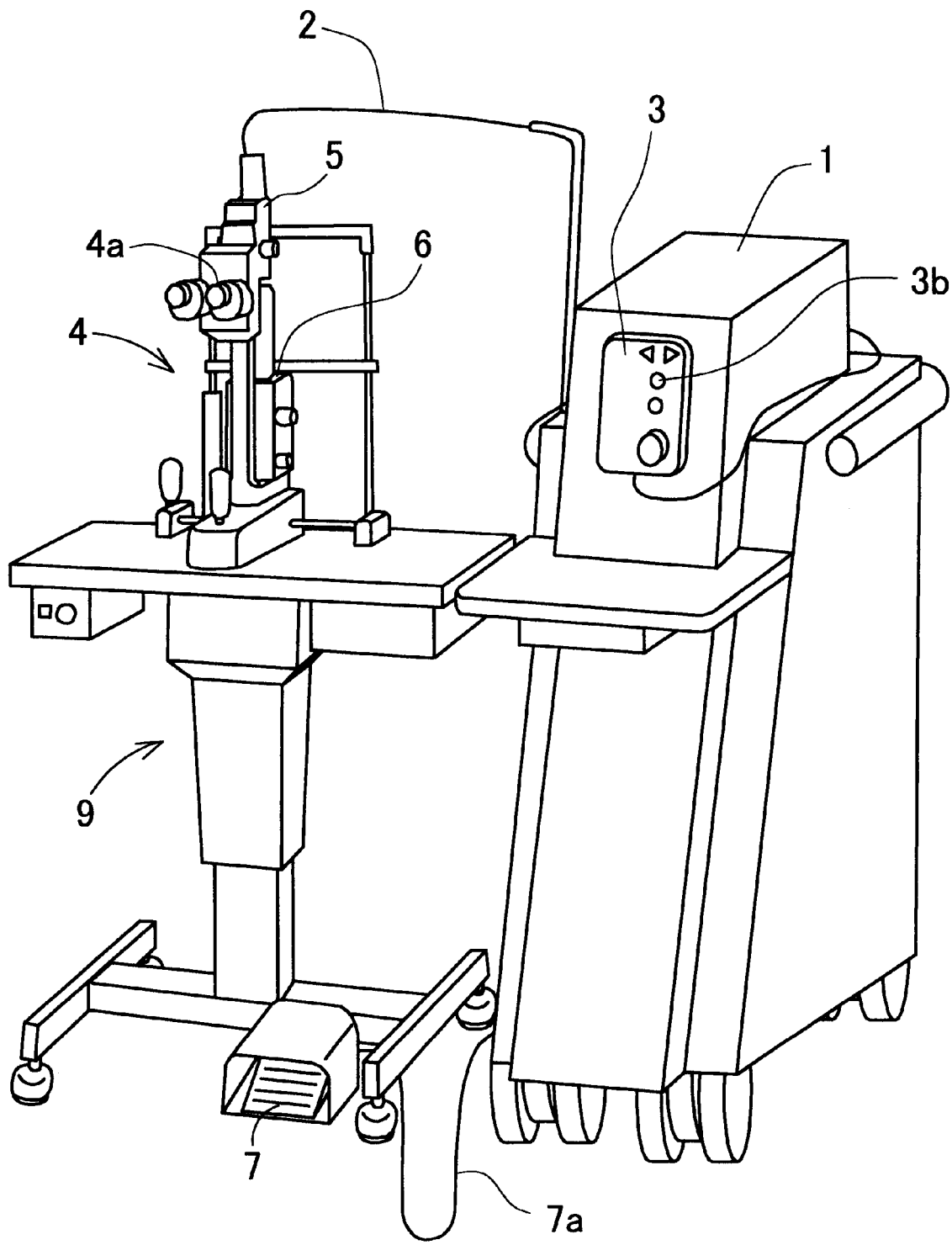
FIG. 1 is a schematic perspective view of a laser treatment apparatus in an embodiment according to the present invention.

A detailed description of a preferred embodiment of a laser treatment apparatus embodying the present invention will now be given referring to the accompanying drawings. FIG. 1 is a schematic perspective view of the laser treatment apparatus for performing laser photocoagulation on a patient's eye.

Numeral 1 is a main unit of the apparatus, which houses a laser source which emits a laser beam for treatment (hereinafter, referred to as a treatment beam), a laser source which emits a laser beam for aiming (hereinafter, referred to as an aiming beam), and an optical system for making the laser beams incident to an optical fiber 2. Numeral 3 is a control box which allows setting of laser irradiation conditions, displaying thereof, and others. Numeral 3b is a selection switch or button for switching an operating mode of the apparatus between a STANDBY mode and a READY mode. The STANDBY mode indicates an operating mode in which the treatment beam is not irradiated even when a footswitch 7 is pressed. The READY mode indicates another operating mode in which a shutter is moved out upon press of the footswitch 7, thereby enabling irradiation of the treatment beam.

Numeral 4 is a slit-lamp delivery through which the treatment beam is irradiated to an affected part of the patient's eye while an operator is allowed to observe the eye. This slit-lamp delivery 4 is provided with a laser irradiating section 5 for irradiating the treatment beam (and the aiming beam) that has been delivered into the optical fiber 2, an illumination section 6 for slit-illuminating the patient's eye, and a binocular microscopic section 4a. Numeral 9 is a stand which mounts thereon the slit-lamp delivery 4; 7, a footswitch for generating a trigger signal to start laser irradiation; and 7a, a cable which connecting the footswitch 7 to the main unit 1.

Figure 2:
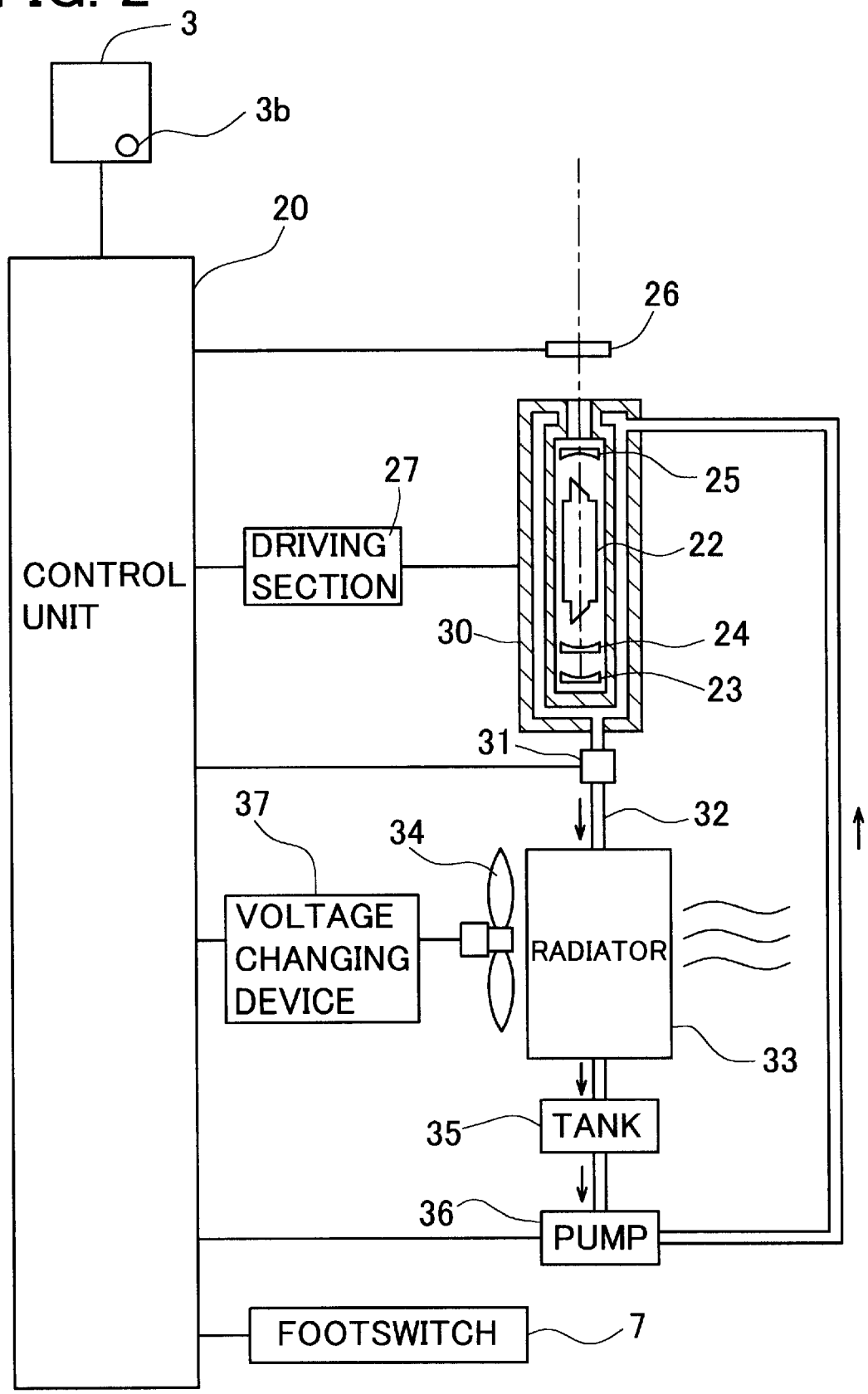
FIG. 2 is a block diagram of a schematic structure of a control system of the apparatus.

FIG. 2 is a block diagram showing a schematic structure of a control system of the apparatus.

Numeral 20 is a control unit for controlling the apparatus. Numeral 30 is a laser head of the laser source that emits the treatment beam. The laser head 30 is internally provided with a laser tube 22 of an ion laser, a first full-reflection mirror 23, a second full-reflection mirror 24, and an output mirror 25. In the present embodiment, as the laser tube, a krypton (Kr) laser having oscillation lights; a red light (647.1 nm), a yellow light (568.2 nm), and a green light (530.9 nm, 520.8 nm) is used. The first full-reflection mirror 23 has the property of reflecting the yellow light (568.2 nm) and the green light (530.9 nm, 520.8 nm), which is fixedly disposed on the optical path (optical axis) of the laser beams. The second full-reflection mirror 24 has the property of reflecting the red light (647.1 nm), which is removably disposed on the optical path. The output mirror 25 has a transmittance of 1–3% with respect to all the wavelength regions of the red, yellow, and green lights. Therefore, when the second full-reflection mirror 24 is placed on the optical path, it constitutes a resonator in cooperation with the output mirror 25, thus oscillating a red treatment beam (647.1 nm). When the second mirror 24 is withdrawn out of the optical path, on the other hand, the first full-reflection mirror 23 constitutes a resonator in cooperation with the output mirror 25, thus oscillating of a yellow treatment beam (568.2 nm) and a green treatment beam (530.9 nm, 520.8 nm).

Numeral 26 is a shutter for intercepting the optical path of the treatment beam emitted from the laser head 30. This shutter 26 is moved out of the optical path when the READY mode is established by means of the selection switch 3b. Numeral 27 is a driving section of the laser head 30. This driving section 27 is controlled by the control unit 20 to supply power to the laser tube 22 for laser oscillation. When the footswitch 7 is pressed in the READY mode, the treatment beam is emitted and delivered to the fiber 2 through an optical system not shown.

Figure 3:
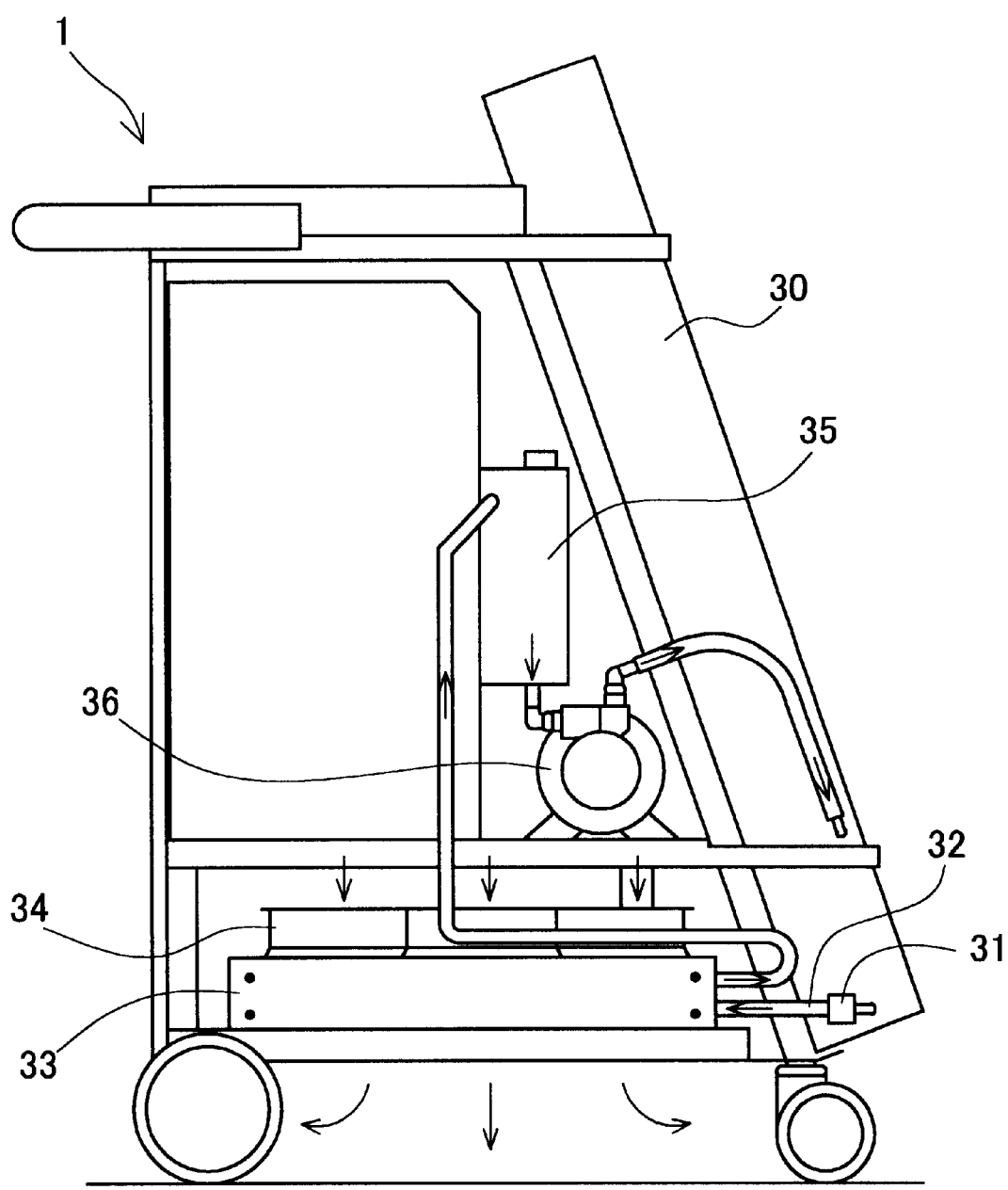
FIG. 3 is a schematic structural view of a cooling mechanism in the apparatus.

Next, the structure of the cooling mechanism (unit) is explained with reference to FIGS. 2 and 3. The laser head 30 is internally formed with a route (pipe) for circulating the cooling water. The cooling water is allowed to circulate through the laser head 30 by the power of a pump 36, thereby cooling the laser head 30. The cooling water that has circulated through the head 30 is then sent to a radiator 33 through a drainpipe 32. At a midpoint in the drainpipe 32, the water temperature sensor 31 is arranged to measure the temperature of the cooling water which has increased in temperature due to the circulation through the laser head 30. The electric fan 34 is mounted on the radiator 33 connected to the drainpipe 32. The fan 34 sends air to cool the cooling water with an increased temperature. After cooled in the radiator 33, the cooling water is stored in a tank 35. Then, the cooling water stored in the tank 35 is sent to the laser head 30 again by the power of the pump 36. The above circulation is repeated. It is to be noted that the water temperature sensor 31, a voltage changing device 37 for driving the electric fan 34, and the pump 36 are connected to the control unit 20.

The operation of the apparatus having the above structure is described below. At first, a brief explanation is made on laser photocoagulation treatment. The environment in which the laser treatment apparatus is installed is a quiet place controlled at a relatively constant temperature, such as rooms for treatment and for outpatients in ophthalmological clinics or hospitals.

Upon turn-on of the power of the main unit 1 with a switch not shown, the apparatus is put in the STANDBY mode. The operator instructs the patient to stably fix his/her eye, and observes the affected part on the fundus of the patient's eye illuminated by slit light while looking at the eye through the microscopic section 4a of the slit-lamp delivery 4. The operator sets in advance laser irradiation conditions (photocoagulation conditions) such as selection of a wavelength of the treatment beam, laser output power, and photocoagulation time, etc. by operation of the switches on the control box 3. Upon completion of preparation for laser irradiation, the selection switch 3b is used to switch the operating mode of the apparatus from the STANDBY mode to the READY mode.

The operator performs alignment using the aiming beam with respect to the affected part and then presses the footswitch 7 to send a trigger signal to the control unit 20. In response to the trigger signal, the control unit 20 causes the driving section 27 to supply the needed electric current to the laser tube 22 to perform laser oscillation, while moves the shutter 26 out of the optical path. Thus, the treatment beam emitted from the laser head 30 is delivered to the slit lamp delivery 4 (the laser irradiating section 5), irradiating the fundus of the patient's eye to photocoagulate the affected part.

Next, the operation of the cooling mechanism is explained. When the power to the main unit 1 is turned on, the control unit 20 supplies the electric current to the laser tube 22 through the driving section 27, causing laser oscillation, with the shutter 26 closed, thereby conducting self diagnosis (test oscillation) in order to provide stable laser output power. In the READY state, the control unit 20 supplies an electric current of about 5A which enables stable discharge for excitation so that laser oscillation can be performed in quick response to the trigger signal. In this way, at other times besides laser oscillation, the laser head 30 is allowed to generate heat from the time when the power to the apparatus is turned on. The control unit 20 thus drives the pump 36 to circulate the cooling water, thereby cooling the laser head 30.

During the laser oscillation (photocoagulation treatment), an electric current of 15A or more is supplied through the driving section 27. Under standard conditions, laser irradiation is carried out with about 100–400 shots for every one disease case. This further increases the heat generation in the laser head 30 during laser oscillation.

The cooling water of an increased temperature due to circulation through the laser head 30 dissipates heat in the radiator 33. This radiator 33 is exposed to the air blown by the fan 34, enhancing a waste-heat effect. That is to say, the fan 34 operates to send the air inside the apparatus to the radiator 33 and discharge the air absorbing the heat out of the apparatus.

The temperature of the cooling water absorbing the heat generated in the laser head 30 is constantly measured or detected by the water temperature sensor 31. Data on the measured water temperatures is transmitted to the control unit 20. In accordance with a rise in the water temperature, the control unit 20 increases the rotational speed of the fan 34 in order to suppress the heat generation of the laser head 30, thereby placing the apparatus in a laser oscillation enabled state. In the present apparatus, the control unit 20 controls the voltage changing device 37 to switch the voltage for driving the fan 34 when the temperature of drained water reaches a predetermined temperature or more set in advance, thereby to increase the rotational speed of the fan 34.

Figure 4:
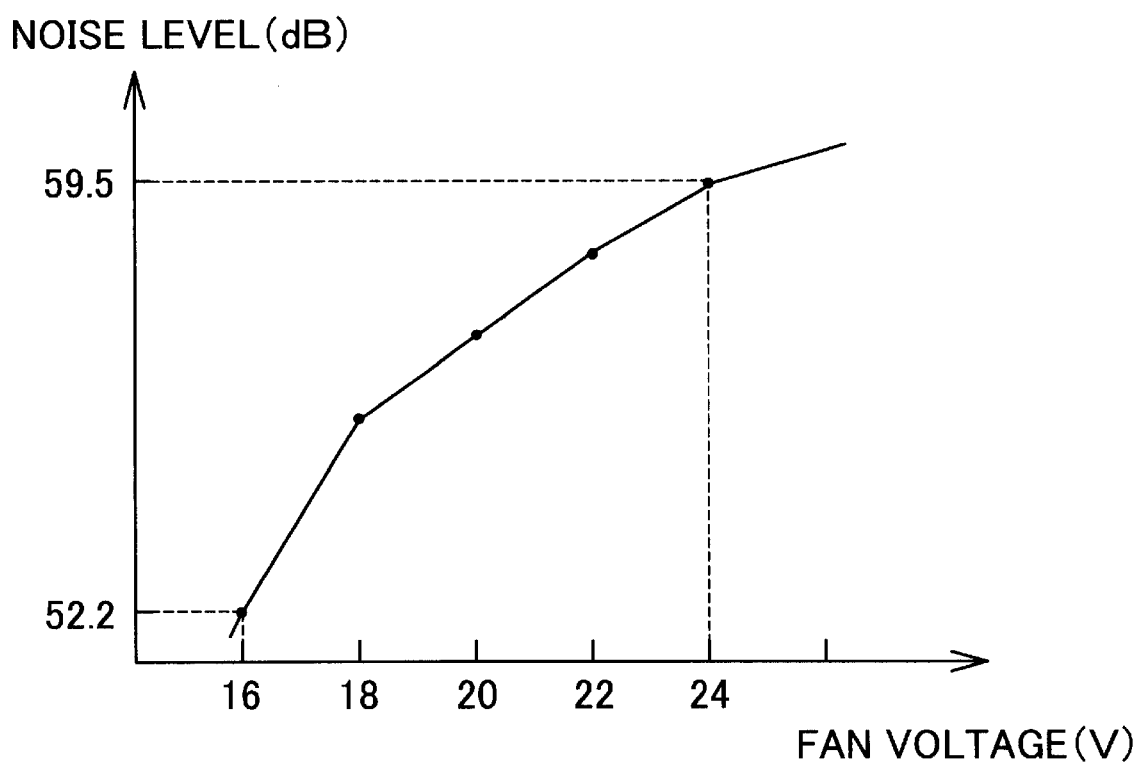
FIG. 4 is a graph showing a relation between fan voltages and noise levels.

FIG. 4 is a graph showing a relation between fan voltage whereby the fan 34 is driven and noise values (levels). Measurements on the noise levels were performed with the fan voltage set to 16V, 18V, 20V, 22V, and a maximum voltage of 24V, respectively. The noise levels were measured at a distance of about 1 meter from the main unit 1 on its left and at a height of about 50 cm above floor level.

The measurements were actually carried out with RION general noise level meter NA29 to measure AP noise levels of an equivalent noise level (Leq) for three seconds. AT this time, the background noise in the measurement room was 39 dB.

As seen in the graph, the noise levels suddenly rose as the fan voltage increased. The fan noise was larger than expected even at middle to low rotational regions of the fan voltage, 18–22 V. A dash-single-dot line in FIG. 5 indicates a measurement result by a conventional control method in which the rotational speed of the fan (namely, the fan voltage) is linearly changed in proportion to the rise in temperature of the cooling water; it is linearly changed to 20V at 25° C. and the maximum 24V at 50° C. According to such the conventional method, if a 10° C. rise in the temperature from 30° C. is caused during laser irradiation of 400 shots, the fan voltage is increased with corresponding high noise.

Figure 5:
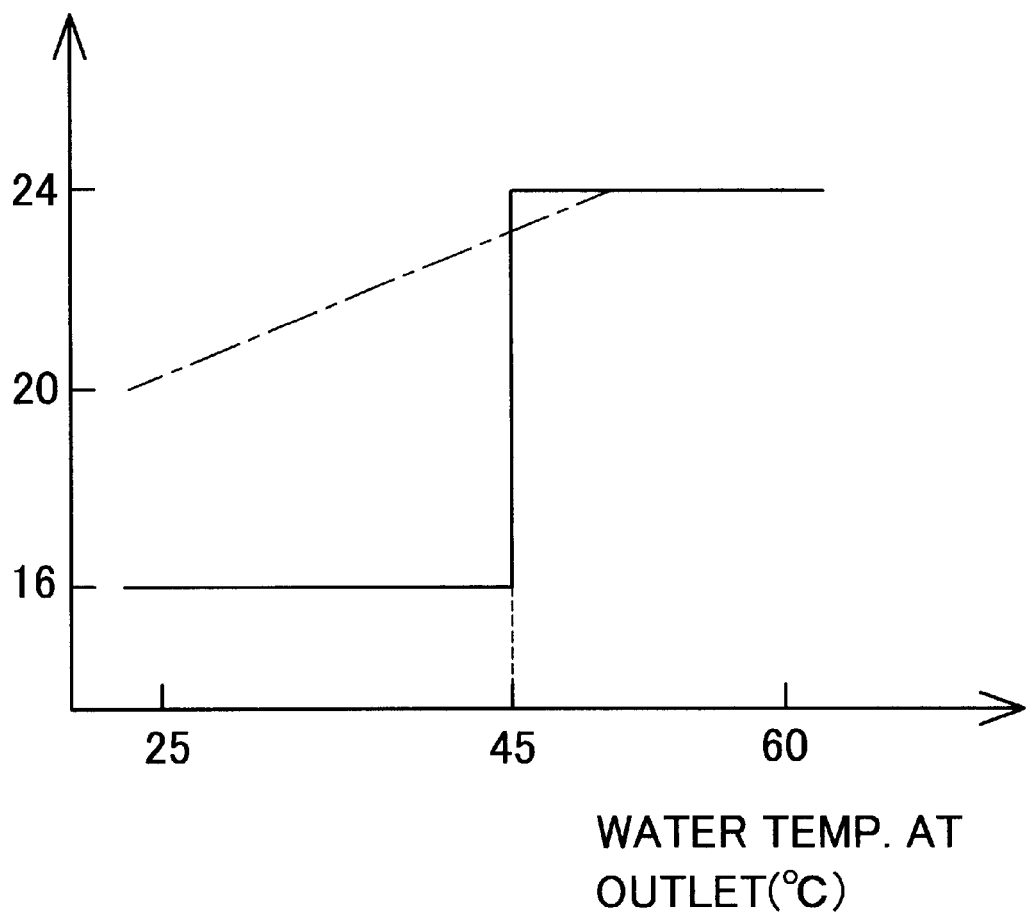
FIG. 5 is a graph showing a relation between temperatures of a cooling water at an outlet and fan voltages.

To reduce the noise, the apparatus in the present embodiment is constructed such that the fan voltage is maintained at a minimum voltage of 16V as shown by a solid line in FIG. 5 until the temperature of drained water from the laser head 30 rises to 45° C. to cause the fan to rotate at low rotational speed, thereby preventing the occurrence of noise. When the temperature of drained water reaches 45° C. or more, the fan voltage is changed to a maximum voltage of 24V to cause the fan to rotate at high rotational speed to thereby enhance a cooling effect.

As above, when the fan voltage is set to the minimum of 16V, the noise level can be controlled at 52.2 dB (FIG. 4). The noise at a level below 53 dB is inaudible to a patient in an operating room. Accordingly, the apparatus can eliminate the anxiety of the patient due to the noise.

It is to be noted that the temperatures to change the fan voltage in the present embodiment were determined in the following manner. FIG. 6 is a table of results of measurements on cooling capability according to differences in temperatures at which the fan voltage was changed from 16V to 24V. The voltage change temperatures for the measurements were set to 40° C., 45° C., and 50° C., different from the linear control in the conventional method. The measurements were conducted in continuous irradiation at intervals of 0.2 sec. Measured items were the time from a drained-water temperature of 30° C. to overheating and the number of shots irradiated for the time, the times needed for cooling the drained water from the overheating to 40° C., 35° C., and 30° C., respectively. It is found from the table that the temperature at which the fan voltage is changed without a significant decrease in cooling capability as compared in the conventional linear control method and as high as possible is 45° C.

In the present embodiment, an overheating temperature of the cooling water is prescribed as 65° C. This is because the cooling water at temperatures exceeding 65° C. may cause a durability problem with the laser oscillator and a change in pressure of krypton gas. In other words, a sealing O-ring and other members made of plastic constituting the laser oscillator may become deformed due to the high temperatures.

The present invention may be embodied in other specific forms without departing from the spirit or essential characteristics thereof. For instance, the numerals such as the fan voltage values and the change temperatures in the above embodiment are only examples and may be appropriately determined according to structures of the laser apparatus and the cooling mechanism.

The above embodiment exemplifies the case of internal circulation water-cooled type which indirectly detects the temperature of the laser head based on the rise in temperature of the cooling water. In the other case of a forced-air-cooled type having a radiating fin, a temperature sensor may be provided in a position where the temperature of the laser head can be directly detected.

As described above, according to the present invention, noises by the cooling fan can be reduced to improve a treatment environment.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus for performing treatments on an affected part of an eye by irradiating the affected part with a laser beam for treatment, the apparatus including:
    a laser oscillator which emits the laser beam for treatment;
    a cooling unit including a fan which cools the laser oscillator, the fan being driven at a first constant speed and a second constant speed, the second constant speed higher than the first constant speed;
    a temperature sensor which directly or indirectly detects a temperature of the laser oscillator;
    a temperature set unit which sets a reference temperature value at which a speed the fan is driven is changed without a significant decrease in cooling capability as compared to a linear temperature control, wherein the reference temperature value is set as high as possible based on a time for the laser oscillator to be heated from a first predetermined temperature to overheating temperature, a number of shots of the laser beam for treatment and a time needed for cooling the laser oscillator from the overheating temperature to a second predetermined temperature; and
    a control unit which drives the fan at the first constant speed while the detected temperature value is lower than the set reference temperature value and at the second constant speed while the detect temperature value is higher than the set reference temperature value.

2. The laser treatment apparatus according to claim 1, wherein the control unit drives the fan at a minimum fan voltage while the detected temperature value is lower than the set reference temperature value and at a maximum fan voltage while the detected temperature value is higher than the set reference temperature value.

3. The laser treatment apparatus according to claim 1, wherein the reference temperature value is set to about 45° C. by the temperature set unit.

4. The laser treatment apparatus according to claim 1, wherein the first constant speed is determined so that a level of noise produced by the fan becomes 53 dB or less.

5. A laser treatment apparatus for performing treatments on an affected part of an eye by irradiating the affected part with a laser beam for treatment, the apparatus including:

a laser oscillator which emits the laser beam for treatment;

a cooling water circulation unit including a pipe and a pump which circulate cooling water through the laser oscillator;

a radiator provided with a fan for making heat radiation of the cooling water, the fan being driven at a first constant speed and a second constant speed, the second constant speed higher than the first constant speed;

a water temperature sensor which detects a temperature of the cooling water drained from the laser oscillator after circulation therethrough;

a temperature set unit which sets a reference temperature value at which a speed the fan is driven is changed without a significant decrease in cooling capability as compared to a linear temperature control, wherein the reference temperature value is set as high as possible based on a time for the laser oscillator to be heated from a first predetermined temperature to overheating temperature, a number of shots of the laser beam for treatment and time needed for cooling the laser oscillator from the overheating temperature to a second predetermined temperature; and a control unit which drives the fan at the first constant speed while the detected temperature value is lower than the set reference temperature value and at the second constant speed while the detect temperature value is higher than the set reference temperature value.

6. The layer treatment apparatus according to claim 5, wherein the control unit drives the fan at a minimum fan voltage while the detected temperature value is lower than the set reference temperature value and at a maximum fan voltage while the detected temperature value is higher than the set reference temperature value.

7. The layer treatment apparatus according to claim 5, wherein the reference temperature value is set to about 45° C. by the temperature set unit.

8. The laser treatment apparatus according to claim 5, wherein the first constant speed is determined so that a level of noise produced by the fan becomes 53 dB or less.

9. A laser treatment apparatus for performing treatments on an affected part by irradiating the affected part with a laser beam for treatment, the apparatus including:

a laser oscillator;

a cooling unit including a fan which cools the laser oscillator;

a temperature sensor which directly or indirectly detects a temperature of the laser oscillator; and a control unit which maintains the fan at a first constant speed when a detected temperature by the temperature sensor is below a predetermined reference value and at a second constant speed when the detected temperature is equal to or more than the predetermined reference value, wherein the second constant speed is higher than the first constant speed, wherein the predetermined reference value is set as high as possible based on a time for the laser oscillator to be heated from a first predetermined temperature to an overheating temperature, a number of shots of the laser beam for treatment and time needed for cooling the laser oscillator from the overheating temperature to a second predetermined temperature.

\* \* \* \* \*